United States Patent [19]
Renauld et al.

[11] Patent Number: 5,830,454
[45] Date of Patent: Nov. 3, 1998

[54] METHOD FOR TREATING CELL MEDIATED AUTOIMMUNE DISORDERS USING INTERLEUKIN-9

[75] Inventors: Jean-Christophe Renauld; Mary-Christine Many, both of Brussels, Belgium

[73] Assignee: Ludwig Institute For Cancer Research, New York, N.Y.

[21] Appl. No.: 706,302

[22] Filed: Aug. 30, 1996

[51] Int. Cl.$^6$ .......................... A61K 38/19; A61K 38/20

[52] U.S. Cl. ........................................................................
424/85.2; 424/85.1; 514/2; 514/12; 514/885; 514/860; 514/813

[58] Field of Search ........................................................
424/85.1, 424/85.2; 514/2, 12, 885, 860, 813

[56] References Cited

PUBLICATIONS

Many et al., "Two–Step Development of Hashimoto–Like Thyroiditis–in Genetically Autoimmune Probe non–obese Diabetic Mice: Effects of Iodine Induced Cell Necorsis", J. Encrinol 147: 311–320, (1995).
Immunology, ed Raitt et al, pp. 13.19 and 23.1–23.11, 1985.
Chybicka, *Acta Hematol Pol* 25(2) Suppl 1, 1994, pp. 21–31.
Elsasser–Berle et al, *Tumor Biol* 14(2) 1993, pp. 69–94.

*Primary Examiner*—Garnette D. Draper
*Attorney, Agent, or Firm*—Felfe & Lynch

[57] ABSTRACT

A method for the treatment of cell mediated autoimmune disease is disclosed. The method involves administering interleukin-9 in an effective amount to the subject. Among the conditions treatable are thyroiditis and autoimmune diabetes.

9 Claims, 2 Drawing Sheets

METHOD FOR TREATING CELL MEDIATED AUTOIMMUNE DISORDERS USING INTERLEUKIN-9

FIELD OF THE INVENTION

This invention relates to the treatment of autoimmune diseases, especially cell mediated autoimmune disorders. In particular, diseases such as thyroiditis and autoimmune diabetes are treatable, via administration of interleukin-9 alone or in combination with other drugs.

BACKGROUND AND PRIOR ART

Interleukin-9 ("IL-9" hereafter), is a glycoprotein which has been isolated from both murine and human cells. See, e.g., U.S. Pat. No. 5,208,218, incorporated by reference. This reference also teaches isolated nucleic acid molecules encoding the protein portion of the molecule, and how to express it.

Various uses of the molecule can be seen in, e.g., U.S. Pat. No. 5,164,317 (proliferation of mast cells); U.S. Pat. Nos. 5,246,701 and 5,132,109 (enhancing production of IgG and inhibiting production of IgE), in addition to its first recognized utility, which is as a T cell growth factor. Exemplary of the vast scientific literature on the molecule are Van Snick, et al, J. Exp. Med. 169(1): 363–368 (1989) (cDNA for the murine molecule, then referred to as P40). Houssiau, et al, J. Immunol 148(10): 3147–3151 (1992) (IL-2 dependence of IL-9 expression in T lymphocytes). Renauld, et al, Oncogene 9(5): 1327–1332 (1994) (effect on thymic lymphomas); Renauld, et al, Blood 85(5): 1300–1305 (1995) (anti-apoptotic factor for thymic lymphoma). Review articles may be found at, e.g., Renauld, et al, Cancer Invest 11(5) 635–640 (1993); Renauld, et al, Adv. Immunol 54: 79–97 (1993).

There is no literature on the influence of IL-9 on autoimmune disorders.

The art is familiar with a vast number of autoimmune disorders, which are classified in various ways. One way of classification is by way of the aspect of the immune system most intimately involved with the disorder. For example, in humoral response associated autoimmune diseases, B cells are involved. Antibodies are generated against self molecules, such as the acetylcholine receptor (myasthenia gravis), or the TSH receptor (Graves disease). In autoimmune diseases involving a cellular response, T cells, macrophages, and NK cells react with self molecules. Exemplary of these conditions are insulin dependent diabetes and thyroiditis. This family of diseases result, inter alia, in a skewing of Th1/Th2 balance.

One problem in the study of autoimmune diseases is the absence of suitable animal models. Without an appropriate system for studying a particular condition, one cannot draw conclusions as to the potential efficacy of a given drug in a therapeutic context.

An appropriate animal model for cell mediated diseases does exist, however, and it has been used in the disclosure which follows. Using the specific case of induced thyroiditis in a murine model, it has now been shown that IL-9 has therapeutic efficacy in Th1 associated autoimmune disorders. This will be shown in the detailed description of preferred embodiments which follows.

DETAILED DESCRIPTION OF PREFERRED EMBODIMENTS

EXAMPLE 1

Figure 1A:
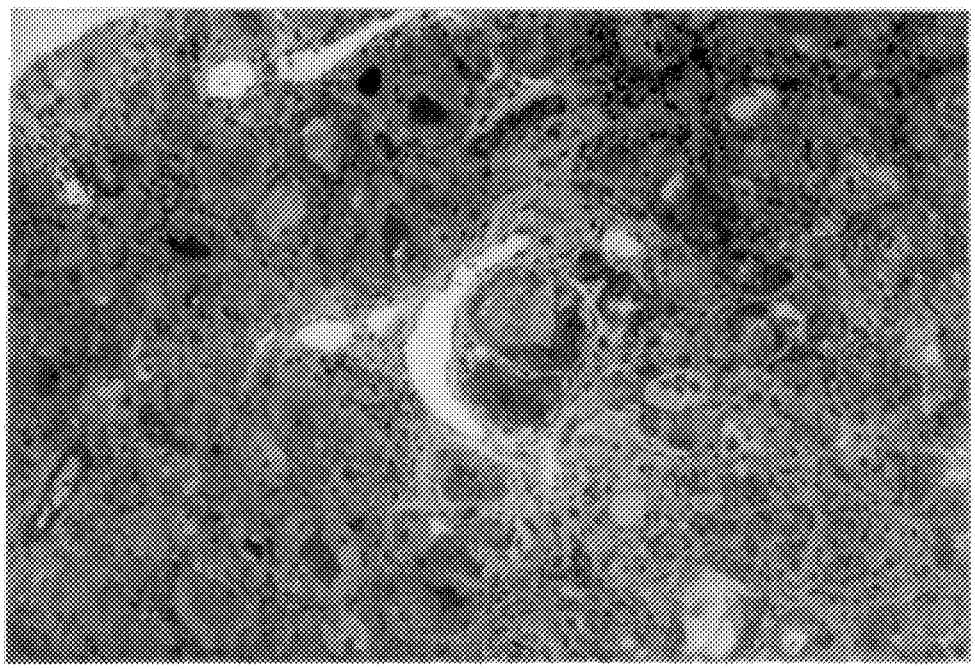
FIG. 1A shows effect of high doses of iodide following induction of goiter.
Figure 1B:
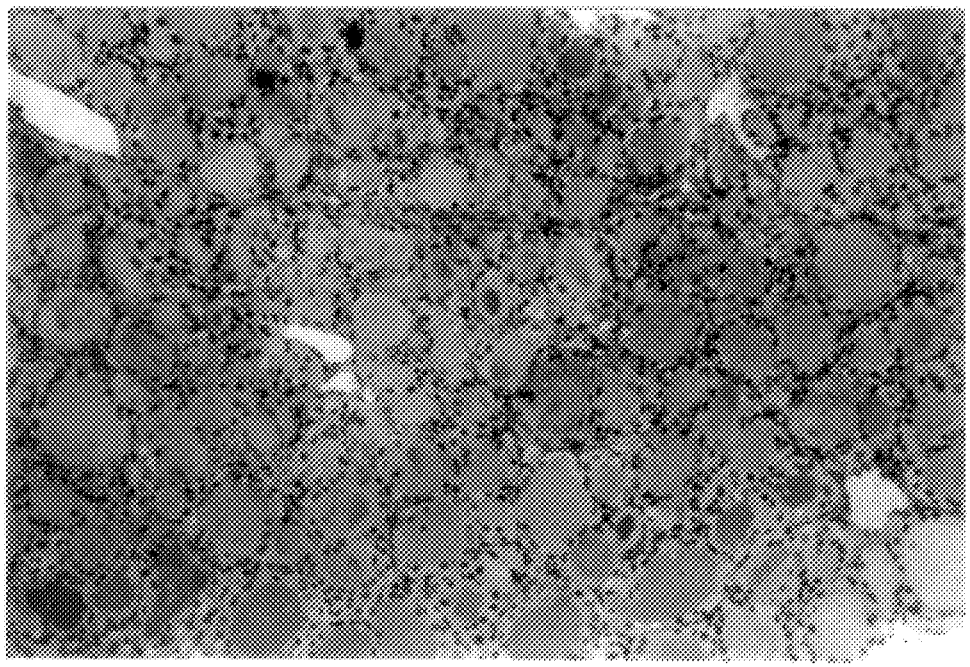
FIG. 1B shows the effect of IL-9 on iodide treated mice.

Two strains of mice, i.e., the FVB strain, and the NOD strain, were used in the experiments which follow. The NOD strain of mice is recognized as an appropriate model for studies on human diseases. This is because the strain is a non-obese, diabetic mouse, which spontaneously develops pancreatic and thyroid lesions resulting from autoimmune disorders, such as diabetes. The mice are also useful as a model for cell mediated autoimmune diseases. See, e.g., Many, et al, J. Endrocrinol 147: 311–320 (1995); Male, et al, Advanced Immunology Third Edition (1996). pg. 12.15; Kikutani, et al, Adv. Immunol 51: 285–322 (1992) all of which are incorporated by reference.

Th1 cells are involved in the process of inflammation of islets of Langerhans in the pancreas, which is a condition associated with diabetes. Many, et al, supra, suggest that the same mechanism is involved in thyroiditis. Hence, the NOD strain is an appropriate model for the work which follows.

Two month old female NOD mice (haplotype H-2g) were used, as were two month old female FVB mice (haplotype H-2q), as a control. The FVB mice can be treated with iodine to develop transient thyroiditis, while the NOD mice develop a persistent form of the condition. Also, the intensity of $CD4^+$ T cell infiltration in affected organs differs. See infra.

Mice were made goitrous by feeding them a low iodine diet (0.1 ug iodine per day), supplemented with 0.25% propylthiouracil for 10 days, followed by the low iodine diet for another 2 days. They then received high doses of iodine (10 ug/day), via intraperitoneal injection, for 4 days. Five mice from each strain also received lug/day of murine interleukin-9, for 6 days. The interleukin-9 was administered in 0.2 ml/volume of PBS via intraperitoneal injection, starting 2 days before the high iodine diet was administered. In controls, only PBS was administered.

Following treatment, mice were anaesthetized with an intraperitoneal injection of 7.5 mg of Nembutal, diluted with saline solution 1/3. Blood samples were collected to measure thyroxin levels via a radio immunoassay, and then the thyroid glands were removed. One lobe of each gland was designated for morphological and stereological analysis, and the other for immunohistochemical analysis.

To carry out the former, lobes were immersed for 2 hours in 2.5% glutaraldehyde in 0.1M cacodylate buffer, post fixed for 1 hour in 1% osmium tetroxide, and embedded in resin. Sections were cut to 0.5 um thickness, and were stained with toluidine blue. Relative volumes of the various glandular components were measured with a projection microscope.

Immunohistochemical analysis was carried out by quick freezing lobes in isopentane cooled in liquid nitrogen. Cryostat sections were taken, and used for immuno peroxidase staining, following Toussaint-Demylle, et al Autoimmunity 7:51–62 (1990), using a monoclonal antibody specific for $CD4^+$ T cells, and one specific for B cells.

Numbers of the cell types (CD4+, B+) were evaluated via magnification (X250), in ten microscopic fields chosen at random from thyroid sections.

The results from these experiments are presented in FIG. 1, and Tables 1 and 2, which are discussed infra.

FIG. 1A shows that administration of a high dose of iodide after goitrogenic treatment had a strong necrotic effect on thyroid cells. Cell debris accumulated into the follicular lumina. After 4 days of treatment, cell necrosis was associated to the interstitial infiltration of inflammatory cells.

After the 6 days of IL-9 administration to the iodide treated FVB mice, the histology of the thyroid was very similar to what was obtained with a high iodine diet alone. See FIG. 1B. Signs of cell necrosis and of thyroiditis were evident, and analysis suggested that the IL-9 aggravated the interstitial infiltration of inflammatory cells. The relative volume of the interstitium was higher than in those control mice (FVB mice), which were not treated with IL-9. See Table 1.

Figure 1C:
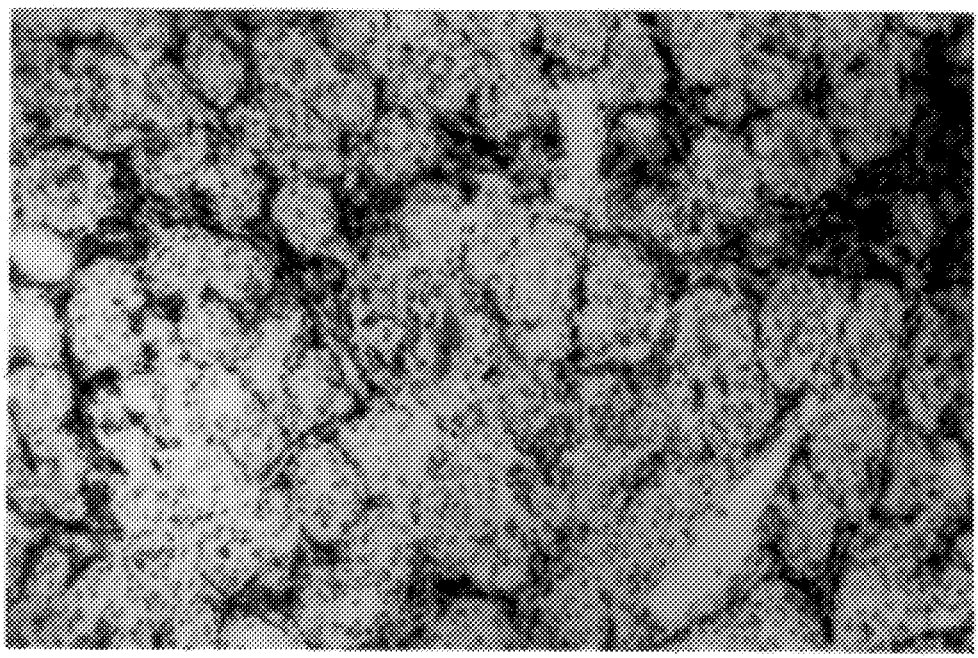
FIG. 1C depicts prevention of thyroid induced thyroiditis in goitrous NOD mice.
Figure 1D:
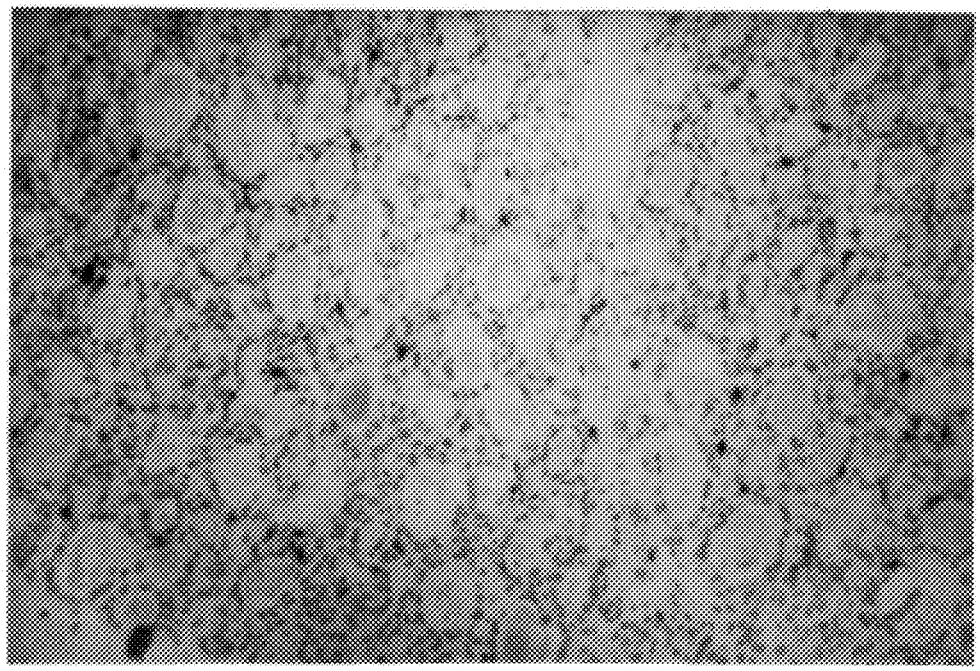
FIG. 1D sets forth results of pathological investigations of these tissues.

In FIG. 1C, it can be seen that in the case of the goitrous NOD mice, all the follicular lumina were filled with necrotic debris, and the interstitium was extensively infiltrated by inflammatory cells. In contrast to the FVB mice, administration of IL-9 to the goitrous NOD mice prevented thyroid-induced thyroiditis. FIG. 1D shows that the large follicular lumina contained little necrotic debris, and few inflammatory cells were found in the interstitium. Table 1 shows that its relative volume was significantly decreased after IL-9 treatment. The relative volumes of epithelium and colloid were increased, as compared to mice which had not received the IL-9. A significant drop in thyroid weight was also observed after administration of the IL-9.

With respect to immunohistochemical analysis, the cells which infiltrated the thyroids of goitrous FVB mice treated with the iodide for 4 days were mainly MHC-Class II positive APCs, as well as T cells. $CD4^+$ T helper cells predominated in this group. The administration of IL-9 increased the number of $CD4^+$ cells, but increased the number of B cells even moreso. See Table 2.

In contrast, administration of iodide to NOD mice resulted in infiltration of numerous $CD4^+$ T cells, and few B cells. When IL-9 was administered, the number of infiltrating $CD4^+$ cells was drastically reduced. See Table 2.

TABLE 1

Mean (±SD, n=5) thyroid weight (mg) and relative volumes (%) of the various glandular components of the thyroids of goitrous FVB and NOD mice treated with iodide alone or plus IL9

| | Thyroid weight | Epithelium | Relative volumes colloid | Interstitium |
|---|---|---|---|---|
| FVB mice goiter+ HID 4 days | 5.8±0.4 | 55.8±5.5 | 17.2±2.4 | 27.0±3.7 |
| FVB mice goiter+ HID 4 days+ IL9 6 days | 5.9±0.5 | 46.8±3.9* | 18.8±1.1 | 34.4±4.1* |
| NOD mice goiter+ HID 4 days | 7.3±0.4+ | 45.9±2.9+ | 15.4±5.1 | 38.7±5.7+ |
| NOD mice goiter+ HID 4 days+ IL9 6 days | 4.5±0.7o+ | 54.1±3.6o+ | 32.0±3.1o+ | 13.8±1.9o+ |

+$p<0.05$:FVB mice treated with IL9 vs. non injected mice.
o$p<0.05$:NOD mice treated with IL-9 vs. non injected mice.
+$p<0.05$:NOD mice vs FVB mice similarly treated.

TABLE 2

Mean (±SD, n=5) numbers of CD4+T cells and B 220+B cells per ten follicular profiles in thyroids of goitrous FVB and NOD mice treated with iodide alone or plus IL9

| | CD4+ T cells | B 220+ B cells |
|---|---|---|
| FVB mice goiter+ HID 4 days | 3.53±0.8 | 2.05±0.2 |
| FVB mice goiter+ HID 4 days+ IL9 6 days | 7.97±1.3* | 10.3±0.8* |
| NOD mice goiter+ HID 4 days | 46.6±5.3+ | 3.4±0.8+ |
| NOD mice goiter+ HID 4 days+ IL9 6 days | 2.9±0.3o+ | 1.3±0.1o+ |

+$p<0.05$:FVB mice treated with IL9 vs non injected mice
o$p<0.05$:NOD mice treated with IL9 vs non injected mice
+$p<0.05$:NOD mice vs FVB mice similarly treated An analysis of thyroxin content in plasma showed levels to be nearly the same. Non-IL-9-injected mice had levels of 2.4±0.08 ng/ml, while mice who had received injections of IL-9 showed levels of 2.2±0.6 ng/ml.

EXAMPLE 2

An additional study was carried out on a murine model for pancreas insulitis. Specifically, using the model, supra, the pancreas of mice were examined following 6 days of administration of IL-9. In the results which follow, the values are the percentage of islets of Langerhans showing signs of insulitis and show that IL-9 reduced this percentage.

| | Iodide Only (5 mice) | Iodide & IL-9 (5 mice) |
|---|---|---|
| Exp. 1 | 41.14±8.05 | 10.9±4.56 |
| Exp. 2 | 38.5±2.4 | 11.5±1.2 |

The foregoing data show that, in an appropriate animal model, IL-9 was effective in treating an autoimmune pathology associated with the thyroid gland, i.e., thyroidititis and with diabetes. As was pointed out, supra, the model used (the NOD mouse), is one which is also used in the study of other autoimmune pathologies, such as autoimmune diabetes, and other cell mediated autoimmune diseases. Hence, one aspect of the invention is a method for treating a cell mediated autoimmune disorder, such as thyroiditis or autoimmune diabetes, via the administration of an effective amount of IL-9. The dosing regimen may vary, depending on the subject and the severity of the condition. In general, however, a dose of from about 500 ng to about 50 ug/kg of body weight of the subject, administered daily, is preferred; preferably, a dose of from about 1 ug to about 10 ug/kg of body weight is administered daily. The IL-9 may be naturally occurring, or recombinant in source, and may or may not be glycosylated. The cytokine can be administered via any standard therapeutic modality, such as via intravenous, intraperitoneal, sublingual, intradermal, subcutaneous, oral, or other forms of administration. The IL-9 may be administered alone, or in combination with pharmaceutically acceptable carriers, adjuvants, diluents, etc. Further, the IL-9 may be combined with one or more therapeutically effective material for treatment of autoimmune disorders. Many drugs are used to treat diabetes, thyroiditis, and other cell mediated autoimmune disorders, such as IL-4. See, e.g., Rapoport, et al, J. Exp. Med. 178: 87–99 (1993). The IL-9 may be combined with these in pharmaceutical compositions and/or kits, wherein the therapeutically active IL-9 and the second drug may be combined (such as a composition), or in kit form, wherein separate portions of the drugs are made available for mixing at the convenience of the physician, patient, etc.

Other aspects of this invention will be clear to the skilled artisan and need not be discussed further.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. Method for treating a cell mediated autoimmune disease selected from the group consisting of autoimmune diabetes and thyroiditis, comprising administering to a subject in need thereof an amount of interleukin 9 sufficient to treat said cell mediated autoimmune disease.

2. The method of claim 1, wherein said cell mediated autoimmune disease is autoimmune diabetes.

3. The method of claim 1, wherein said cell mediated autoimmune disease is thyroiditis.

4. The method of claim 1, wherein said interleukin-9 is administered in an amount sufficient to reduce the number of $CD4^+$ cells in said subject.

5. The method of claim 1, wherein said interleukin 9 is human interleukin 9.

6. The method of claim 1, wherein said interleukin-9 is produced recombinantly.

7. The method of claim 1, wherein said interleukin-9 is administered intravenously, intraperitoneally, transdermally, subcutaneously, orally, or sublingually.

8. The method of claim 1, further comprising administering a cell mediated autoimmune disease associated specific drug.

9. The method of claim 1, comprising administering said interleukin 9 in an amount from about 500 ng to about 50 ug/kg of body weight.

* * * * *

UNITED STATES PATENT AND TRADEMARK OFFICE
CERTIFICATE OF CORRECTION

PATENT NO. : 5,830,454
DATED : Nov. 3, 1998
INVENTOR(S) : Renauld et al.

It is certified that error appears in the above-identified patent and that said Letters Patent is hereby corrected as shown below:

On the cover, in the section entitled References Cited, Publications, line 4, change "Encrinol" to - - Endocrinol. - -.
In column 3, Table 1, column 1, in each instance, move the "+" symbols to the start of the next line.
In column 4, Table 2, column 1, in each instance, move the "+" symbols to the start of the next line.

Signed and Sealed this

Fifth Day of September, 2000

Q. TODD DICKINSON

*Attest:*

*Attesting Officer*  *Director of Patents and Trademarks*